(12) United States Patent
Salaam-Zayid et al.

(10) Patent No.: US 12,203,219 B2
(45) Date of Patent: *Jan. 21, 2025

(54) FIBROUS STRUCTURES COMPRISING A SURFACTANT

(71) Applicant: The Procter & Gamble Company, Cincinnati, OH (US)

(72) Inventors: Latisha Evette Salaam-Zayid, Cincinnati, OH (US); Jose Enrique Betancourt, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/874,437

(22) Filed: Jul. 27, 2022

(65) Prior Publication Data

US 2022/0380982 A1 Dec. 1, 2022

Related U.S. Application Data

(63) Continuation of application No. 16/200,911, filed on Nov. 27, 2018, now Pat. No. 11,401,662.

(60) Provisional application No. 62/599,233, filed on Dec. 15, 2017.

(51) Int. Cl.
| | |
|---|---|
| *D21H 21/24* | (2006.01) |
| *A61K 8/02* | (2006.01) |
| *A61K 8/37* | (2006.01) |
| *A61K 8/44* | (2006.01) |
| *A61Q 19/10* | (2006.01) |
| *B31F 1/07* | (2006.01) |
| *B31F 1/12* | (2006.01) |
| *B31F 1/16* | (2006.01) |
| *D21H 11/04* | (2006.01) |
| *D21H 17/14* | (2006.01) |
| *D21H 27/00* | (2006.01) |
| *D21H 27/02* | (2006.01) |
| *D21H 27/30* | (2006.01) |
| *D21H 27/40* | (2006.01) |

(52) U.S. Cl.
CPC .......... *D21H 21/24* (2013.01); *A61K 8/0208* (2013.01); *A61K 8/37* (2013.01); *A61K 8/442* (2013.01); *A61Q 19/10* (2013.01); *B31F 1/07* (2013.01); *B31F 1/12* (2013.01); *B31F 1/16* (2013.01); *D21H 11/04* (2013.01); *D21H 17/14* (2013.01); *D21H 27/002* (2013.01); *D21H 27/02* (2013.01); *D21H 27/30* (2013.01); *D21H 27/40* (2013.01)

(58) Field of Classification Search
CPC ........ D21H 21/24; D21H 17/14; D21H 21/22; D21H 27/002; D21H 27/02; D21H 27/30; D21H 11/04; D21H 17/40; A61K 8/0208; A61K 8/37; A61K 8/442; C08J 2207/12; Y10T 442/60; A61Q 19/10; B31F 1/07; B31F 1/12; B31F 1/16

See application file for complete search history.

(56) References Cited

U.S. PATENT DOCUMENTS

| | | | |
|---|---|---|---|
| 4,721,647 A | 1/1988 | Nakanishi et al. | |
| 4,959,125 A * | 9/1990 | Spendel ................ | D21H 17/28 162/111 |
| 5,102,738 A | 4/1992 | Bell et al. | |
| 6,261,679 B1 | 7/2001 | Chen et al. | |
| 6,475,501 B1 * | 11/2002 | Kelly ..................... | A01N 59/06 424/402 |
| 6,488,943 B1 | 12/2002 | Beerse et al. | |
| 6,603,054 B2 | 8/2003 | Chen et al. | |
| 7,365,030 B2 | 4/2008 | Chamba et al. | |
| 7,988,826 B2 | 8/2011 | Inaoka et al. | |
| 8,545,861 B2 * | 10/2013 | Baumoller ............. | D21H 21/22 424/404 |
| 8,586,015 B2 * | 11/2013 | Panandiker ............ | C11D 3/373 424/70.28 |
| 8,613,836 B2 | 12/2013 | Sealey et al. | |
| 10,260,201 B2 | 4/2019 | Sealey et al. | |
| 10,415,190 B2 | 9/2019 | Jiang et al. | |
| 10,513,827 B2 | 12/2019 | Sealey et al. | |
| 10,697,123 B2 * | 6/2020 | Chen ...................... | D21H 21/24 |
| 10,895,022 B2 * | 1/2021 | Barnholtz ............. | D21H 13/00 |
| 11,401,662 B2 * | 8/2022 | Salaam-Zayid ........ | A61Q 19/10 |
| 11,618,977 B2 * | 4/2023 | Barnholtz ............... | D04H 1/56 428/401 |
| 2001/0024716 A1 | 9/2001 | Chen et al. | |
| 2002/0148583 A1 * | 10/2002 | Baumoller ............. | D21H 21/24 162/158 |
| 2003/0097964 A1 | 5/2003 | Holmberg et al. | |
| 2003/0220039 A1 | 11/2003 | Chen et al. | |
| 2005/0009431 A1 | 1/2005 | Chamba et al. | |
| 2008/0073045 A1 | 3/2008 | Dyer et al. | |
| 2008/0216977 A1 | 9/2008 | Dyer et al. | |
| 2008/0254081 A1 | 10/2008 | Schroeder et al. | |
| 2009/0104430 A1 | 4/2009 | Cordial et al. | |

(Continued)

FOREIGN PATENT DOCUMENTS

| | | |
|---|---|---|
| EP | 0713860 A1 | 5/1996 |
| WO | 2011017532 A2 | 2/2011 |

OTHER PUBLICATIONS

All Office Actions, U.S. Appl. No. 16/200,911.

*Primary Examiner* — Jose A Fortuna
(74) *Attorney, Agent, or Firm* — James E. Oehlenschlager

(57) ABSTRACT

Fibrous structures, for example sanitary tissue products, such as toilet tissue, having one or more neat surfactant components on at least one exterior surface, methods for making same, and methods for removing fecal matter from a user's skin are provided.

19 Claims, No Drawings

(56) References Cited

U.S. PATENT DOCUMENTS

| | | |
|---|---|---|
| 2010/0212849 A1 | 8/2010 | Smith et al. |
| 2011/0129645 A1 | 6/2011 | Dyer et al. |
| 2012/0213725 A1 | 8/2012 | Galleguillos et al. |
| 2014/0102650 A1 | 4/2014 | Qin et al. |
| 2015/0094252 A1 | 4/2015 | Cuyubamba et al. |
| 2015/0140273 A1* | 5/2015 | Qin ................... B32B 5/022 428/152 |
| 2016/0160445 A1 | 6/2016 | Sealey et al. |
| 2016/0304818 A1 | 10/2016 | Cordial et al. |
| 2018/0094388 A1* | 4/2018 | Mohammadi .......... D21H 27/40 |
| 2018/0320318 A1 | 11/2018 | Qin et al. |
| 2019/0002747 A1* | 1/2019 | Salaam-Zayid ........ A61Q 19/00 |
| 2019/0186078 A1* | 6/2019 | Salaam-Zayid ........ A61Q 19/10 |
| 2020/0080031 A1 | 3/2020 | Dani et al. |
| 2022/0380982 A1* | 12/2022 | Salaam-Zayid ........ D21H 27/40 |
| 2023/0220630 A1* | 7/2023 | McKee ................ D21H 27/002 162/129 |

\* cited by examiner

FIBROUS STRUCTURES COMPRISING A SURFACTANT

FIELD OF THE INVENTION

The present invention relates to fibrous structures, for example sanitary tissue products, such as toilet tissue, comprising one or more neat surfactant components, methods for making same and methods for removing fecal matter from a user's skin.

BACKGROUND OF THE INVENTION

Fecal residue left behind during a bowel movement cleaning event leads to consumer discomfort around feeling clean and fresh. This discomfort can escalate to feelings of fear, shame and incompetence, due to the presence of residual soil (fecal matter) and the sensorial impacts that result from the residual fecal matter; namely, lack of a fresh feel on a user's skin during and/or after a bowel movement.

The physiological tactile sensation and sensory perception of what is clean and fresh continues to be an untapped, undefined, and unmet need for consumers of sanitary tissue products, such as toilet tissue.

Some users of fibrous structures, for example sanitary tissue products, such as toilet tissue, desire better experiences with their toilet tissue, especially with respect to feeling clean of fecal matter, including residual fecal matter.

Accordingly, one problem faced by formulators of fibrous structures, for example sanitary tissue products, such as toilet tissue, is providing fibrous structures that provide an improved clean feeling to a consumer, for example after wiping one's skin, for example anal skin, with the fibrous structures such that the consumer experiences an acceptable and/or pleasant physiological tactile sensation and/or sensory perception of being clean and/or fresh, for example having more fecal matter, for example residual fecal matter removed during wiping.

There is a need for a fibrous structure, for example sanitary tissue product, such as a toilet tissue, comprising one or more neat surfactant components that delivers improved fecal matter removal compared to know fibrous structures and/or a consumer acceptable and/or consumer desirable sensation, for example as a result of improved removal of fecal matter such as residual fecal matter, and methods for making such fibrous structure.

SUMMARY OF THE INVENTION

The present invention fulfills the needs described above by providing a fibrous structure, for example a sanitary tissue product, such as a toilet tissue, comprising one or more neat surfactant components that deliver improved fecal matter removal compared to known fibrous structures.

One solution to the problem described above is to provide a fibrous structure, for example a sanitary tissue product, such as a toilet tissue, comprising one or more neat surfactant components, such as a neat cocoamidopropyl betaine, that results in a user of such a fibrous structure experiencing a pleasant and/or desirable physiological tactile sensation and/or sensory perception after contacting the user's skin with such a fibrous structure and/or improved removal of fecal matter, such as residual fecal matter.

In one example of the present invention, a fibrous structure comprising a one or more neat surfactant components, for example present on at least a portion of an exterior surface of the fibrous structure, is provided.

In yet another example of the present invention, a method for making a fibrous structure, the method comprising the step of applying one or more neat surfactant components, such as cocoamidopropyl betaine, is provided.

In even yet another example of the present invention, a single- or multi-ply sanitary tissue product comprising one or more fibrous structures of the present invention, is provided.

In still another example of the present invention, a method for improving the removal of fecal matter, for example residual fecal matter from a user's skin, the method comprising the step of contacting a user's skin, for example anal skin, with a fibrous structure comprising one or more neat surfactant components, such as cocoamidopropyl betaine, is provided.

The present invention provides a fibrous structure, for example a sanitary tissue product, such as toilet tissue, comprising one or more neat surfactant components, methods for making same, and a method for removing fecal matter, such as residual fecal matter from a user's skin.

DETAILED DESCRIPTION OF THE INVENTION

"Sanitary tissue product" as used herein means a soft, low density (i.e. <about 0.15 g/cm$^3$) article comprising one or more fibrous structure plies according to the present invention, wherein the sanitary tissue product is useful as a wiping implement for post-urinary and post-bowel movement cleaning (toilet tissue), for otorhinolaryngological discharges (facial tissue), and multi-functional absorbent and cleaning uses (absorbent towels). The sanitary tissue product may be convolutedly wound upon itself about a core or without a core to form a sanitary tissue product roll.

The sanitary tissue products and/or fibrous structures of the present invention may exhibit a basis weight of greater than 15 g/m$^2$ to about 120 g/m$^2$ and/or from about 15 g/m$^2$ to about 110 g/m$^2$ and/or from about 20 g/m$^2$ to about 100 g/m$^2$ and/or from about 30 to 90 g/m$^2$. In addition, the sanitary tissue products and/or fibrous structures of the present invention may exhibit a basis weight between about 40 g/m$^2$ to about 120 g/m$^2$ and/or from about 50 g/m$^2$ to about 110 g/m$^2$ and/or from about 55 g/m$^2$ to about 105 g/m$^2$ and/or from about 60 to 100 g/m$^2$.

The sanitary tissue products of the present invention may exhibit a sum of MD and CD dry tensile strength of greater than about 59 g/cm (150 g/in) and/or from about 78 g/cm to about 394 g/cm and/or from about 98 g/cm to about 335 g/cm. In addition, the sanitary tissue product of the present invention may exhibit a sum of MD and CD dry tensile strength of greater than about 196 g/cm and/or from about 196 g/cm to about 394 g/cm and/or from about 216 g/cm to about 335 g/cm and/or from about 236 g/cm to about 315 g/cm. In one example, the sanitary tissue product exhibits a sum of MD and CD dry tensile strength of less than about 394 g/cm and/or less than about 335 g/cm.

In another example, the sanitary tissue products of the present invention may exhibit a sum of MD and CD dry tensile strength of greater than about 196 g/cm and/or greater than about 236 g/cm and/or greater than about 276 g/cm and/or greater than about 315 g/cm and/or greater than about 354 g/cm and/or greater than about 394 g/cm and/or from about 315 g/cm to about 1968 g/cm and/or from about 354 g/cm to about 1181 g/cm and/or from about 354 g/cm to about 984 g/cm and/or from about 394 g/cm to about 787 g/cm.

The sanitary tissue products of the present invention may exhibit an initial sum of MD and CD wet tensile strength of less than about 78 g/cm and/or less than about 59 g/cm and/or less than about 39 g/cm and/or less than about 29 g/cm.

The sanitary tissue products of the present invention may exhibit an initial sum of MD and CD wet tensile strength of greater than about 118 g/cm and/or greater than about 157 g/cm and/or greater than about 196 g/cm and/or greater than about 236 g/cm and/or greater than about 276 g/cm and/or greater than about 315 g/cm and/or greater than about 354 g/cm and/or greater than about 394 g/cm and/or from about 118 g/cm to about 1968 g/cm and/or from about 157 g/cm to about 1181 g/cm and/or from about 196 g/cm to about 984 g/cm and/or from about 196 g/cm to about 787 g/cm and/or from about 196 g/cm to about 591 g/cm.

The sanitary tissue products of the present invention may exhibit a density (based on measuring caliper at 95 g/in$^2$) of less than about 0.60 g/cm$^3$ and/or less than about 0.30 g/cm$^3$ and/or less than about 0.20 g/cm$^3$ and/or less than about 0.10 g/cm$^3$ and/or less than about 0.07 g/cm$^3$ and/or less than about 0.05 g/cm$^3$ and/or from about 0.01 g/cm$^3$ to about 0.20 g/cm$^3$ and/or from about 0.02 g/cm$^3$ to about 0.10 g/cm$^3$.

The sanitary tissue products of the present invention may be in the form of sanitary tissue product rolls. Such sanitary tissue product rolls may comprise a plurality of connected, but perforated sheets of fibrous structure, that are separably dispensable from adjacent sheets.

In another example, the sanitary tissue products may be in the form of discrete sheets that are stacked within and dispensed from a container, such as a box.

The fibrous structures and/or sanitary tissue products of the present invention may comprise additives such as surface softening agents, for example silicones, quaternary ammonium compounds, aminosilicones, lotions, and mixtures thereof, temporary wet strength agents, permanent wet strength agents, bulk softening agents, wetting agents, latexes, especially surface-pattern-applied latexes, dry strength agents such as carboxymethylcellulose and starch, and other types of additives suitable for inclusion in and/or on sanitary tissue products.

"Fibrous structure" as used herein means a structure that comprises one or more fibers and/or filaments. In one example, a fibrous structure at least comprises a plurality of fibers. In one example, the fibrous structure may comprise a plurality of wood pulp fibers. In another example, the fibrous structure may comprise a plurality of non-wood pulp fibers, for example plant fibers, synthetic staple fibers, and mixtures thereof. In still another example, in addition to pulp fibers, the fibrous structure may comprise a plurality of filaments, such as polymeric filaments, for example thermoplastic polymer filaments such as polyolefin filaments (i.e., polypropylene filaments) and/or hydroxyl polymer filaments, for example polyvinyl alcohol filaments and/or polysaccharide filaments such as starch filaments. In one example, a fibrous structure according to the present invention means an orderly arrangement of fibers alone and with filaments within a structure in order to perform a function. Non-limiting examples of fibrous structures of the present invention include paper.

Non-limiting examples of processes for making fibrous structures include known wet-laid papermaking processes and air-laid papermaking processes. Such processes typically include steps of preparing a fiber composition, oftentimes referred to as a fiber slurry in wet-laid processes, either wet or dry, and then depositing a plurality of fibers onto a forming wire or belt such that an embryonic fibrous structure is formed, drying and/or bonding the fibers together such that a fibrous structure is formed, and/or further processing the fibrous structure such that a finished fibrous structure is formed. For example, in typical papermaking processes, the finished fibrous structure is the fibrous structure that is wound on the reel at the end of papermaking, but before converting thereof into a sanitary tissue product.

Non-limiting types of fibrous structures according to the present invention include conventionally felt-pressed fibrous structures; pattern densified fibrous structures; and high-bulk, uncompacted fibrous structures. The fibrous structures may be of a homogeneous or multilayered ("layered" meaning two or three or more layers) construction; and the sanitary tissue products made therefrom may be of a single-ply or multi-ply construction.

The fibrous structures may be post-processed, such as by embossing and/or calendaring and/or folding and/or printing images thereon.

The fibrous structures may be through-air-dried fibrous structures or conventionally dried fibrous structures.

The fibrous structures may be creped or uncreped. In one example, the fibrous structures may be belt-creped and/or fabric creped.

Non-limiting examples of processes for making fibrous structures include known wet-laid papermaking processes, for example conventional wet-pressed papermaking processes and through-air-dried papermaking processes, and air-laid papermaking processes. Such processes typically include steps of preparing a fiber composition in the form of a suspension in a medium, either wet, more specifically aqueous medium, or dry, more specifically gaseous, i.e. with air as medium. The aqueous medium used for wet-laid processes is oftentimes referred to as a fiber slurry. The fibrous slurry is then used to deposit a plurality of fibers onto a forming wire, fabric, or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, often referred to as a parent roll, and may subsequently be converted into a finished product, e.g. a single- or multi-ply sanitary tissue product.

The fibrous structures of the present invention may be homogeneous or may be layered. If layered, the fibrous structures may comprise at least two and/or at least three and/or at least four and/or at least five layers of fiber and/or filament compositions.

In one example, the fibrous structure of the present invention consists essentially of fibers, for example pulp fibers, such as cellulosic pulp fibers and more particularly wood pulp fibers.

In another example, the fibrous structure of the present invention comprises fibers and is void of filaments.

In still another example, the fibrous structures of the present invention comprises filaments and fibers, such as a co-formed fibrous structure.

"Co-formed fibrous structure" as used herein means that the fibrous structure comprises a mixture of at least two different materials wherein at least one of the materials comprises a filament, such as a polypropylene filament, and at least one other material, different from the first material, comprises a solid additive, such as a fiber and/or a particulate. In one example, a co-formed fibrous structure comprises solid additives, such as fibers, such as wood pulp fibers, and filaments, such as polypropylene filaments.

"Fiber" and/or "Filament" as used herein means an elongate particulate having an apparent length greatly exceeding its apparent width, i.e. a length to diameter ratio of at least about 10. In one example, a "fiber" is an elongate particulate as described above that exhibits a length of less than 5.08 cm (2 in.) and a "filament" is an elongate particulate as described above that exhibits a length of greater than or equal to 5.08 cm (2 in.).

Fibers are typically considered discontinuous in nature. Non-limiting examples of fibers include pulp fibers, such as wood pulp fibers, and synthetic staple fibers such as polyester fibers.

Filaments are typically considered continuous or substantially continuous in nature. Filaments are relatively longer than fibers. Non-limiting examples of filaments include meltblown and/or spunbond filaments. Non-limiting examples of materials that can be spun into filaments include natural polymers, such as starch, starch derivatives, cellulose and cellulose derivatives, hemicellulose, hemicellulose derivatives, and synthetic polymers including, but not limited to polyvinyl alcohol filaments and/or polyvinyl alcohol derivative filaments, and thermoplastic polymer filaments, such as polyesters, nylons, polyolefins such as polypropylene filaments, polyethylene filaments, and biodegradable or compostable thermoplastic fibers such as polylactic acid filaments, polyhydroxyalkanoate filaments and polycaprolactone filaments. The filaments may be monocomponent or multicomponent, such as bicomponent filaments.

In one example of the present invention, "fiber" refers to papermaking fibers. Papermaking fibers useful in the present invention include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified fibrous structure. U.S. Pat. Nos. 4,300,981 and 3,994,771 are incorporated herein by reference for the purpose of disclosing layering of hardwood and softwood fibers. Also applicable to the present invention are fibers derived from recycled paper, which may contain any or all of the above categories as well as other non-fibrous materials such as fillers and adhesives used to facilitate the original papermaking.

Natural papermaking fibers useful in the present invention include animal fibers, mineral fibers, plant fibers, and mixtures thereof. Animal fibers may, for example, be selected from the group consisting of: wool, silk, and mixtures thereof. Plant fibers may, for example, be derived from a plant selected from the group consisting of: wood, cotton, cotton linters, flax, sisal, abaca, hemp, hesperaloe, jute, bamboo, bagasse, kudzu, corn, sorghum, gourd, agave, loofah, and mixtures thereof. In one example the fibers comprise trichomes, such as trichomes obtained from *Stachys* bzyantina, for example trichomes from a Lamb's Ear plant.

Wood fibers; often referred to as wood pulps include chemical pulps, such as kraft (sulfate) and sulfite pulps, as well as mechanical and semi-chemical pulps including, for example, groundwood, thermomechanical pulp, chemi-mechanical pulp (CMP), chemi-thermomechanical pulp (CTMP), neutral semi-chemical sulfite pulp (NSCS). Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified and/or layered fibrous structure. U.S. Pat. Nos. 4,300,981 and 3,994,771 are incorporated herein by reference for the purpose of disclosing layering of hardwood and softwood fibers. Also applicable to the present invention are fibers derived from recycled paper, which may contain any or all of the above categories as well as other non-fibrous materials such as fillers and adhesives used to facilitate the original papermaking.

The wood pulp fibers may be short (typical of hardwood fibers) or long (typical of softwood fibers). Non-limiting examples of short fibers include fibers derived from a fiber source selected from the group consisting of: Acacia, *Eucalyptus*, Maple, Oak, Aspen, Birch, Cottonwood, Alder, Ash, Cherry, Elm, Hickory, Poplar, Gum, Walnut, Locust, Sycamore, Beech, *Catalpa, Sassafras, Gmelina, Albizia, Anthocephalus*, and *Magnolia*. Non-limiting examples of long fibers include fibers derived from Pine, Spruce, Fir, Tamarack, Hemlock, Cypress, and Cedar. Softwood fibers derived from the kraft process and originating from more-northern climates may be preferred. These are often referred to as northern softwood kraft (NSK) pulps.

Synthetic fibers may be selected from the group consisting of: wet spun fibers, dry spun fibers, melt spun (including melt blown) fibers, synthetic pulp fibers, and mixtures thereof. Synthetic fibers may, for example, be comprised of cellulose (often referred to as "rayon"); cellulose derivatives such as esters, ether, or nitrous derivatives; polyolefins (including polyethylene and polypropylene); polyesters (including polyethylene terephthalate); polyamides (often referred to as "nylon"); acrylics; non-cellulosic polymeric carbohydrates (such as starch, chitin and chitin derivatives such as chitosan); and mixtures thereof.

"Ply" or "Plies" as used herein means an individual finished fibrous structure optionally to be disposed in a substantially contiguous, face-to-face relationship with other plies, forming a multiple ply finished fibrous structure product and/or sanitary tissue product. It is also contemplated that a single fibrous structure can effectively form two "plies" or multiple "plies", for example, by being folded on itself.

"Surface of a fibrous structure" and/or "surface of sanitary tissue product" as used herein means that portion of the fibrous structure and/or sanitary tissue product that is exposed to the external environment. In other words, the surface of a fibrous structure and/or surface of a sanitary tissue product is that portion of the fibrous structure and/or sanitary tissue product that is not completely surrounded by other portions of the fibrous structure and/or sanitary tissue product.

"User Contacting Surface" as used herein means that portion of the fibrous structure and/or surface softening composition and/or lotion composition present directly and/or indirectly on the surface of the fibrous structure that is exposed to the external environment. In other words, it is that surface formed by the fibrous structure including any neat surfactant component and/or surface softening composition and/or lotion composition present directly and/or indirectly on the surface of the fibrous structure that contacts an opposing surface when used by a user. For example, it is that surface formed by the fibrous structure including any neat surfactant component and/or surface softening composition and/or lotion composition present directly and/or indirectly on the surface of the fibrous structure that contacts a user's skin, for example a user's anal skin or skin surrounding a user's anal region, when a user wipes his/her skin, for example after a bowel movement, with the fibrous structure of the present invention.

In one example, the user contacting surface, especially for a textured and/or structured fibrous structure, such as a through-air-dried fibrous structure and/or an embossed fibrous structure, may comprise raised areas and recessed areas of the fibrous structure. In the case of a through-air-dried, pattern densified fibrous structure the raised areas may be knuckles and the recessed areas may be pillows and vice versa. Accordingly, the knuckles may, directly and/or indirectly, comprise the neat surfactant component and/or the surface softening composition and/or lotion composition and the pillows may be void of the neat surfactant component and/or the surface softening composition and/or the lotion composition and vice versa so that when a user contacts the user's skin with the fibrous structure, only the lotion composition contacts the user's skin. A similar case is true for embossed fibrous structures where the embossed areas may, directly and/or indirectly, comprise the neat surfactant component and/or the surface softening composition and/or the lotion composition and the non-embossed areas may be void of the neat surfactant component and/or the surface softening composition and/or the lotion composition and vice versa.

The user contacting surface may be present on the fibrous structure and/or sanitary tissue product, for example toilet tissue before use by the user and/or the user contacting surface may be created/formed prior to and/or during use of the fibrous structure and/or sanitary tissue product, for example toilet tissue by the user, such as upon the user applying pressure to the fibrous structure and/or sanitary tissue product, for example toilet tissue as the user contacts the user's skin with the fibrous structure and/or sanitary tissue product, for example toilet tissue.

"Neat Surfactant Component" as used herein means that the surfactant component is free from admixture and/or dilution and/or encapsulation and/or emulsion. In one example, a neat surfactant component is a neat surfactant not mixed or adulterated with any other substance, for example is not part of an emulsion, for example not an aqueous emulsion, and/or is not encapsulated within an encapsulating material and/or is not mixed with any other matter, excluding other neat surfactants. A neat surfactant component may comprise two or more neat surfactants.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Fibrous Structures

The fibrous structures according to the present invention comprise a surface, for example a user contacting surface, comprising one or more neat surfactant components.

In one example, the fibrous structure according to the present invention comprises a surface, for example a user contacting surface, comprising a neat surfactant component, for example a surface softening composition, comprising a surface softening agent and one or more neat surfactant components.

In another example, the surface of the fibrous structure may comprise a layer of a neat surfactant components and/or a surface softening composition according to the present invention and a layer of a different neat surfactant components and/or surface softening composition and/or a lotion composition. The layers of the neat surfactant components and/or surface softening compositions and/or lotion composition may be phase registered with one another. In another example, the different neat surfactant components and/or surface softening compositions and/or lotion composition may cover different regions of the surface of the fibrous structure, for example they may be in a striped or patterned configuration.

In still another example, the neat surfactant components and/or surface softening composition of the present invention may cover about 100% and/or greater than 98% and/or greater than 95% and/or greater than 90% of the surface area of the surface, for example the user contacting surface of the fibrous structure.

The neat surfactant component and/or surface softening composition and/or lotion composition may be applied to a surface, for example a user contacting surface of the fibrous structure by any suitable means known in the art. Any contact or contact-free application suitable for applying the neat surfactant component and/or surface softening composition and/or lotion composition, such as spraying, dipping, padding, printing, slot extruding, such as in rows or patterns, rotogravure printing, flexographic printing, offset printing, screen printing, mask or stencil application process, and mixtures thereof can be used to apply the neat surfactant component and/or surface softening composition and/or lotion composition to the surface of the fibrous structure and/or sanitary tissue product, for example toilet tissue. Neat surfactants and/or surface softening compositions can be applied to the fibrous structure and/or sanitary tissue product before, concurrently, or after the lotion composition application to the fibrous structure and/or sanitary tissue product.

In one example, the neat surfactant component and/or the surface softening composition and/or the lotion composition is applied to the surface of the fibrous structure during the fibrous structure making process, such as before and/or after drying the fibrous structure.

In another example, the neat surfactant component and/or the surface softening composition and/or the lotion composition is applied to the surface of the fibrous structure during the converting process.

In yet another example, the neat surfactant component and/or the surface softening composition is applied to the surface of a fibrous structure prior to application of the lotion composition.

The neat surfactant component and/or the surface softening composition and/or lotion composition can be applied during papermaking and/or converting, especially if applied to the outside layer of a layered fibrous structure and/or sanitary tissue product comprising such layered fibrous structure.

The neat surfactant component and/or surface softening composition and/or lotion composition can be applied by separate devices or by a single device that has two or more chambers capable of separately delivering the different compositions, especially incompatible, different compositions, such as the neat surfactant component and/or the surface softening composition and the lotion composition.

The application devices may be sequentially arranged along the papermaking (fibrous structure making) and/or converting process.

The fibrous structure may comprise one or more fibrous structure plies within a single- or multi-ply sanitary tissue product.

In addition to the one or more neat surfactant components and any of the additional components described herein, the fibrous structure may comprise a surface treating composition, for example a surface softening composition, which may comprise one or more additives selected from the group consisting of: surface softening agents, humectants, emollients, immobilizing agents, preservatives, and mixtures thereof.

In one example, the fibrous structure and/or single- or multi-ply sanitary tissue product according to the present invention further comprises a surface treating composition, for example a surface softening composition, such as silicone- and/or quaternary ammonium compound- and/or polyhydroxy compound-containing composition, present between an exterior surface of the fibrous structure and/or sanitary tissue product and a neat surfactant component. In one example, the surface treating composition comprises a silicone, for example a silicone selected from the group consisting of: polydimethylsiloxanes, aminiosilicones, and mixtures thereof. In one example, the surface treating composition comprise a polyhydroxy compound, for example a polyhydroxy compound selected from the group consisting of: polyethylene glycols and mixtures thereof.

In one example the neat surfactant component is present on at least a portion of an exterior surface of the fibrous structure, for example at a level of at least 0.0001% and/or at least 0.001% and/or at least 0.01% and/or at least 0.1% and/or to about 5% and/or to about 2% and/or to about 1% and/or less than 1% and/or less than 0.8% and/or less than 0.5% and/or less than 0.3% by weight of the fibrous structure.

In one example, the exterior surface of the fibrous structure comprises two or more neat surfactant components. In one example, the exterior surface of the fibrous structure comprises a neat surfactant component wherein at least 80% by weight of the neat surfactant component of a first surfactant, for example a neat zwitterionic surfactant such as cocoamidopropyl betaine, and less than 20% by weight of the neat surfactant component of one or more other neat surfactants, for example a neat nonionic surfactant.

In one example, the fibrous structure of the present invention comprises a plurality of fibrous elements, for example filaments and/or fibers. The fibers may comprise pulp fibers, for example wood pulp fibers and/or non-wood pulp fibers. The fibers may comprise synthetic fibers. At least one of the fibrous elements, for example filaments, may comprise a thermoplastic polymer, such as a thermoplastic selected from the group consisting of: polyolefins, polylactates, polyesters, and mixtures thereof, such as polyolefin, for example a polyolefin selected from the group consisting of: polypropylene, copolymers of propylene, polyethylene, copolymers of ethylene, and mixtures thereof. In one example, at least one of the fibrous elements, for example filaments, comprises a hydroxyl polymer, for example a hydroxyl polymer selected from the group consisting of: polyvinyl alcohol, polysaccharides and derivatives thereof, and mixtures thereof. In one example, the hydroxyl polymer comprises a polysaccharide and/or derivatives thereof.

In one example, the fibrous structure is a through-air-dried fibrous structure, for example a through-air-dried fibrous structure that is creped and/or uncreped.

In another example, the fibrous structure is a conventional wet pressed fibrous structure.

In another example, the fibrous structure is a belt creped fibrous structure.

In another example, the fibrous structure is a fabric creped fibrous structure.

In yet another example, the fibrous structure is an embossed, for example an embossed fibrous structure.

In one example, a single- or multi-ply sanitary tissue product comprises a first fibrous structure ply according to the present invention, and a second fibrous structure ply, which may be the same or different as the first fibrous structure ply.

In one example, the fibrous structure of the present invention may be made by a method comprising the step of applying a neat surfactant component to at least a portion of an exterior surface of a fibrous structure.

In one example, the fibrous structure is a bath tissue (for example a fibrous structure that comprises a temporary wet strength agent and/or is void of permanent wet strength and/or is designed to be flushed down toilets), not a paper towel or facial tissue or wipe, for example a multi-ply bath tissue, such as a multi-ply bath tissue roll.

In one example, the fibrous structure, for example sanitary tissue product, may be in the form of a roll. When in the form of a roll, the roll may exhibit a roll compressibility of about 0.5% to about 15%, or about 1.0% to about 12.5% or about 1.0% to about 8%, specifically including all 0.1 increments between the recited ranges as measured according to the Roll Compressibility Test Method described herein. The roll of fibrous structure, for example sanitary tissue product, of the present disclosure may exhibit a roll compressibility of less than about 15% and/or less than about 12.5% and/or less than about 10% and/or less than about 8% and/or less than about 7% and/or less than about 6% and/or less than about 5% and/or less than about 4% and/or less than about 3% to about 0 and/or to about 0.5%, and/or to about 1%, specifically including all 0.1 increments between the recited ranges as measured according to the Roll Compressibility Test Method. The roll of fibrous structure, for example sanitary tissue product, of the present invention may exhibit a roll compressibility of from about 4% to about 10% and/or from about 4% to about 8% and/or from about 4% to about 7% and/or from about 4% to about 6%, specifically including all 0.1 increments between the recited ranges as measured according to the Roll Compressibility Test Method.

When the fibrous structure, for example sanitary tissue product, is in the form of a roll, the roll exhibit a roll bulk of about 4 $cm^3/g$ to about 30 $cm^3/g$ and/or about 6 $cm^3/g$ to about 15 $cm^3/g$, specifically including all 0.1 increments between the recited ranges. The roll of fibrous structure, for example sanitary tissue product, of the present invention may exhibit a roll bulk of greater than about 4 $cm^3/g$ and/or greater than about 5 $cm^3/g$ and/or greater than about 6 $cm^3/g$ and/or greater than about 7 $cm^3/g$ and/or greater than about 8 $cm^3/g$ and/or greater than about 9 $cm^3/g$ and/or greater than about 10 $cm^3/g$ and/or greater than about 12 $cm^3/g$ and/or less than about 20 $cm^3/g$ and/or less than about 18 $cm^3/g$ and/or less than about 16 $cm^3/g$ and/or less than about 14 $cm^3/g$, specifically including all 0.1 increments between the recited ranges.

In one example, a roll of fibrous structure, for example sanitary tissue product, of the present invention may exhibit a roll bulk of greater than 4 $cm^3/g$ and a Roll Compressibility of less than 10% and/or a roll bulk of greater than 6 $cm^3/g$ and a Roll Compressibility of less than 8% and/or a roll bulk of greater than 8 cm³/g and a Roll Compressibility of less than 7% as measured according to the Roll Compressibility Test Method.

The fibrous structure, for example sanitary tissue product, of the present invention may exhibit a roll firmness of about 2.5 mm to about 15 mm and/or about 3 mm to about 13 mm and/or about 4 mm to about 10 mm, specifically including all 0.1 increments between the recited ranges as measured according to the Roll Firmness Test Method described herein.

In one example, the fibrous structure, for example sanitary tissue product, may be in the form of a roll. When in the form of a roll, the roll may exhibit a roll compressibility of about 0.5% to about 15%, or about 1.0% to about 12.5% or about 1.0% to about 8%, specifically including all 0.1 increments between the recited ranges as measured according to the Roll Compressibility Test Method described herein and a roll bulk of about 4 cm³/g to about 30 cm³/g and/or about 6 cm³/g to about 15 cm³/g, specifically including all 0.1 increments between the recited ranges and a roll firmness of about 2.5 mm to about 15 mm and/or about 3 mm to about 13 mm and/or about 4 mm to about 10 mm, specifically including all 0.1 increments between the recited ranges as measured according to the Roll Firmness Test Method described herein.

In one example, the fibrous structure, for example sanitary tissue product, may be in the form of a roll. When in the form of a roll, the roll may exhibit a Roll Compressibility of from about 0.5% to about 15% as measured according to the Roll Compressibility Test Method, a roll bulk of about 4 cm³/g to about 30 cm³/g, and a Roll Firmness of from about 2.5 mm to about 15 mm as measured according to the Roll Firmness Test Method.

In one example, a roll of fibrous structure, for example sanitary tissue product, of the present inventions may exhibit a roll diameter of about 3 inches to about 12 inches and/or about 3.5 inches to about 8 inches and/or about 4.5 inches to about 6.5 inches, specifically including all 0.1 increments between the recited ranges. The roll of fibrous structure, for example sanitary tissue product, of the present invention may exhibit a roll diameter of greater than 4 inches and/or greater than 5 inches and/or greater than 6 inches and/or greater than 7 inches and/or greater than 8 inches, specifically including all 0.1 increments between the recited ranges.

Neat Surfactant Component

The fibrous structure of the present invention comprises a neat surfactant component comprising a neat surfactant and/or two or more neat surfactants, for example mild surfactants. The neat surfactant component comprises neat surfactants suitable for application to the skin, for example anal skin. Suitable neat surfactants for use herein include any known or otherwise effective cleansing surfactant suitable for application to the skin, for example anal skin. These neat surfactants include neat nonionic surfactants, neat anionic surfactants, neat amphoteric surfactants, neat zwitterionic surfactants, neat cationic surfactants, and mixtures thereof. In one example, the neat surfactant component comprises a mixture of at least one neat nonionic surfactant, at least one neat anionic surfactant and at least one neat amphoteric surfactant. In one example, neat surfactants in the general categories of alkyl amines and alkanolamines are generally present, if at all, at minimal levels because such surfactants tend to be less mild than other suitable surfactants. In one example, the fibrous structure of the present invention is substantially free of alkyl amines and/or alkanolamines.

The neat surfactant may be selected from the group consisting of: Polyglyceryl-6 Caprylate; Polyglyceryl-4 Caprate; Polyglyceryl-4 Cocoate; Polyglyceryl-6 Ricinoleate, Capryl/Caparamidopropyl Betaine, and mixtures thereof.

In another example the neat surfactant is selected from the group consisting of: Polyglyceryl-6 Caprylate; Polyglyceryl-4 Caprate; Capryl/Caparamidopropyl Betaine, and mixtures thereof.

In another example, the neat surfactant component comprises a mixture or blend of two or more and/or three or more of the following surfactants: Polyglyceryl-6 Caprylate; Polyglyceryl-4 Caprate; Polyglyceryl-4 Cocoate; Polyglyceryl-6 Ricinoleate. Capryl/Caparamidopropyl Betaine, Coco Glucoside, Decyl Glucoside, Lauryl Glucoside, Sodium Cocoyl Glycinate, Sodium Cocoyl Isethionate, and mixtures thereof.

In another example, the neat surfactant component comprises a mixture or blend of Polyglyceryl-4 Caprate and Capryl/Caparamidopropyl Betaine.

In another example, the neat surfactant component comprises a mixture or blend of Polyglyceryl-6 Caprate and Capryl/Caparamidopropyl Betaine.

In another example, the neat surfactant component comprises a mixture or blend of Polyglyceryl-4 Caprate and Capryl/Caparamidopropyl Betaine.

In another example, the neat surfactant component comprises a mixture or blend of Polyglyceryl-4 Caprate and Polyglyceryl-4 Caprate.

In another example, the neat surfactant component comprises a mixture or blend of Polyglyceryl-4 Caprate, Polyglyceryl-4 Caprate, and Capryl/Caparamidopropyl Betaine.

The neat surfactant and/or neat surfactant component may be added to the fibrous structure at an addition rate of at least 1 #/ton and/or at least 2 #/ton and/or at least 5 #/ton and/or at least 7 #/ton and/or 10 #/ton.

a. Neat Nonionic Surfactants

The fibrous structure of the present invention may comprise at least one neat nonionic surfactant. Non-limiting examples of such neat nonionic surfactants exhibit an HLB from about 1.5 to about 15.0 and/or from about 3.4 to about 15.0 and/or from about 3.4 to about 9.5 and/or from about 3.4 to about 5.0. The balance between the hydrophilic and lipophilic moieties in a surfactant molecule is used as a method of classification (hydrophile-lipophile balance, HLB). The HLB values for commonly-used surfactants are readily available in the literature (eg. Handbook of Pharmaceutical Excipients, The Pharmaceutical Press. London, 1994). The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20.

Non-limiting examples of suitable neat nonionic surfactants for use on the fibrous structures of the present invention and/or in the neat surfactant component are disclosed in McCutcheon's, Detergents and Emulsifiers, North American edition (1986), published by allured Publishing Corporation; and McCutcheon's, Functional Materials, North American Edition (1992);

Non-limiting examples of neat nonionic surfactants for use herein are those selected form the group consisting of: $C_8$-$C_{14}$ glucose amides, $C_8$-$C_{14}$ alkyl polyglucosides, sucrose cocoate, sucrose laurate, and mixtures thereof. In one example, the neat nonionic surfactant is selected from the group consisting of: glyceryl monohydroxystearate, Steareth-2, propylene glycol stearate, PEG-2 stearate, sorbitan monostearate, glyceryl stearate, laureth-2 and mixtures thereof. In one example, the neat nonionic surfactant comprises Steareth-2.

In one example, the neat surfactant may comprise a nonionic surfactant selected from the group consisting of: Decylglucoside, Laureth-(10,23,4), PEG-10SorbitanLaurate, Polysorbate-(20,21,40,60,61,65,80,81), Steareth-(2,10,15,20), Cocamidopropylamine Oxide, and mixtures thereof.

b. Neat Anionic Surfactants

The fibrous structure of the present invention may comprise at least one neat anionic surfactant. In one example, the neat anionic surfactant is selected from the group consisting of: alkyl sulfates, alkyl ether sulfates, alkyl sulfonates, and mixtures thereof.

Non-limiting examples of suitable neat anionic surfactants suitable for use on the fibrous structure of the present invention and/or in the neat surfactant component include alkyl sulfates ("AS") and alkyl ether sulfates ("AES"). These neat anionic surfactants have the formulas $ROSO_3M$ and $RO(C_2H_4O)_xSO_3M$, respectively wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohols having from about 8 to about 24 carbon atoms. In one example, R has from about 10 to about 18 carbon atoms in both the alkyl and alkyl ether sulfates. The alcohols can be derived from fats, e.g., coconut oil or tallow, or can be synthetic. In one example, the alcohols are lauryl alcohol and straight chain alcohols derived from coconut oil. Such alcohols are reacted with about 1 to about 10 and/or from about 3 to about 5 and/or with about 3, molar proportions of ethylene oxide and the resulting mixture of molecular species having, for example, an average of 3 moles of ethylene oxide per mole of alcohol, is sulfated and neutralized.

In one example, the neat alkyl ether sulfates which may be used on the fibrous structure of the present invention and/or in the neat surfactant component include sodium and ammonium salts of coconut alkyl triethylene glycol ether sulfate; tallow alkyl triethylene glycol ether sulfate, and tallow alkyl hexaoxyethylene sulfate. In one example, the neat alkyl ether sulfates comprise a mixture of individual compounds such that the mixture has an average alkyl chain length of from about 10 to about 16 carbon atoms and an average degree of ethoxylation of from about 1 to about 4 moles of ethylene oxide.

Other suitable neat anionic surfactants include water-soluble salts of the organic, sulfuric acid reaction products of the general formula $[R^1—SO_3-M]$, wherein $R^1$ is chosen from the group consisting of: a straight or branched chain, saturated aliphatic hydrocarbon radical having from about 8 to about 24 and/or from about 10 to about 18 carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms and/or from about 10 to about 18 carbon atoms and a sulfonating agent, e.g., $SO_3$, $H_2SO_4$, oleum, obtained according to known sulfonation methods, including bleaching and hydrolysis. In one example, the neat anionic surfactant comprises alkali metal and ammonium sulfonated $C_{10-18}$ n-paraffins.

Other suitable surfactants are described in *McCutcheon's, Emulsifiers and Detergents*, 1989 Annual, published by M. C. Publishing Co., and in U.S. Pat. No. 3,929,678.

In one example, the neat anionic surfactants for use on the fibrous structure of the present invention and/or in the neat surfactant component include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and mixtures thereof.

In one example, the neat anionic surfactants comprise branched alkyl chains such as sodium trideceth sulfate. Mixtures of two or more neat anionic surfactants may be used in some examples.

In one example, the neat surfactant may comprise a neat anionic surfactant selected from the group consisting of: Sodium Cocyl Isethionate, Sodium Lauryl Sulfoacetate, Sodium Socoyl Sarcosinate, Sodium Lauryl Sarcosinate, Sodium Lauroyl Sarcosinate, Ethyl PEG-15 CocamineSulfate, Dioctyl Sodium Sulfosuccinate, Diethylhexyl Sodium Sulfosuccinate, Sodium Lauryl Glucose Carboxylate, Sodium Methyl Cocoylor Lauryl Taurate, Sodium Cocoyl Glycinate, Sodium Lauroyl/cocoyl Glutamate, Sodium Cocoyl Glutamate, and mixtures thereof.

c. Neat Amphoteric Surfactants

The fibrous structure of the present invention may comprise at least one neat amphoteric surfactant.

Non-limiting examples of neat amphoteric surfactants suitable for use on the present invention and/or in the neat surfactant component include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

In one example, the neat surfactant may comprise a neat amphoteric surfactant selected from the group consisting of: Cocamidopropyl Betaine, Coco Betaine Sodium Cocoamphoacetate, Disodium Cocoamphodiacetate, Disodium Cocoamphodipropionate, Sodium Lauroamphoacetate, and mixtures thereof.

Non-limiting examples of neat amphoteric surfactants include amphoacetates and diamphoacetates as described below.

Amphoacetate:

Diamphoacetate:

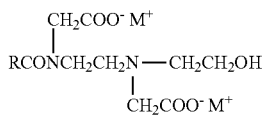

The suitable amphoacetates and diamphoacetates conform to the formulas (above) where R is an aliphatic group of 8 to 18 carbon atoms. $M^+$ is a cation such as sodium, potassium, ammonium, or substituted ammonium. Non-limiting examples of suitable amphoacetates and diamphoacetates include sodium lauroamphoacetate, sodium cocoamphoactetate, disodium lauroamphoacetate, and disodium cocodiamphoacetate and mixtures thereof.

Additional neat surfactants from the classes of neat zwitterionic surfactant and/or neat cationic surfactants may be incorporated into the neat surfactant component and/or onto the fibrous structure of the present invention.

Non-limiting examples of neat zwitterionic surfactants suitable for use on the fibrous structure of the present invention and/or in the neat surfactant component include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

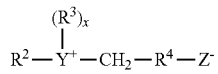

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of: nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of: carboxylate, sulfonate, sulfate, phosphonate, and phosphate groups, and mixtures thereof.

Non-limiting examples of other suitable neat zwitterionic surfactants for use on the fibrous structure of the present invention and/or in the neat surfactant component include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

In one example, the neat surfactant component comprises a neat zwitterionic surfactant, for example cocoamidopropyl betaine.

Surface Treating Composition (for Example Surface Softening Composition)

A surface treating composition, for example a surface softening composition, for purposes of the present invention, is a composition that improves the tactile sensation of a surface of a fibrous structure perceived by a user whom holds a fibrous structure and/or sanitary tissue product comprising the fibrous structure and rubs it across the user's skin. Such tactile perceivable softness can be characterized by, but is not limited to, friction, flexibility, and smoothness, as well as subjective descriptors, such as a feeling like lubricious, velvet, silk or flannel.

The surface softening composition may or may not be transferable. Typically, it is substantially non-transferable.

The surface softening composition may increase or decrease the surface friction of the surface of the fibrous structure, especially the user contacting surface of the fibrous structure. Typically, the surface softening composition will reduce the surface friction of the surface of the fibrous structure compared to a surface of the fibrous structure without such surface softening composition.

The surface softening composition comprises a surface softening agent. The surface softening composition during application to the fibrous structure may comprise at least about 0.1% and/or at least 0.5% and/or at least about 1% and/or at least about 3% and/or at least about 5% to 100% and/or to about 98% and/or to about 95% and/or to about 90% and/or to about 80% and/or to about 70% and/or to about 50% and/or to about 40% by weight of the surface softening agent. In one example, the surface softening composition comprises from about 5% to about 40% by weight of the surface softening agent.

The surface softening composition present on the fibrous structure and/or sanitary tissue product comprising the fibrous structure of the present invention may comprise at least about 0.01% and/or at least about 0.05% and/or at least about 0.1% of total basis weight of the surface softening agent. In one example, the fibrous structure and/or sanitary tissue product may comprise from about 0.01% to about 20% and/or from about 0.05% to about 15% and/or from about 0.1% to about 10% and/or from about 0.01% to about 5% and/or from about 0.1% to about 2% of total basis weight of the surface softening composition.

In one example, the surface softening composition may be present on and/or in the fibrous structure at a level of at least 1 #/ton and/or at least 5 #/ton and/or at least 10 #/ton and/or at least 15 #/ton.

Surface Softening Agents

The surface softening composition may comprise one or more surface softening agents selected from the group consisting of: quaternary ammonium compounds, amines, fatty esters, sucrose esters, silicones, dispersible polyolefins, clays, polysaccharides, fatty acids, softening oils, polymer latexes, polyhydroxy compounds, and mixtures thereof.

In one example, the surface softening agent is selected from the group consisting of: quaternary ammonium compounds, silicone polymers, polysaccharides, clays, amines, fatty esters, dispersible polyolefins, polymer latex, and mixtures thereof. Non-limiting examples of suitable quaternary ammonium compounds include an alkyl quaternary ammonium compound, such as an alkyl quaternary ammonium compound selected from the group consisting of: a mono-alkyl quaternary ammonium compound, a dialkyl quaternary ammonium compound, a trialkyl quaternary ammonium compound, and mixtures thereof. Non-limiting examples of suitable amines include amines selected from the group consisting of: ester amines (monoester amines, diester amines, and/or triester amines), amidoesteramines, amidoamines (monoamido amines and/or diamido amines), imidazoline amines, alkyl amines (mono alkylamines, dialkyl amines quats, and/or trialkyl amines), and mixtures thereof. Non-limiting examples of suitable silicone polymers include silicone polymers selected from the group consisting of: cyclic silicones, polydimethylsiloxanes, aminosilicones, cationic silicones, silicone polyethers, silicone resins, silicone urethanes, and mixtures thereof. A non-limiting example of a suitable polysaccharide includes cationic starch. A non-limiting example of a suitable clay includes smectite clay. Non-limiting examples of suitable dispersible polyolefins include dispersible polyolefins selected from the group consisting of: polyethylene, polypropylene, and mixtures thereof. Non-limiting examples of suitable fatty esters include fatty esters selected from the group consisting of: a polyglycerol ester, a sucrose ester, a glycerol ester, and mixtures thereof.

In one example, the surface softening agent comprises a quaternary ammonium compound selected from the group consisting of: ester quaternary ammonium compounds, (monoesterquats, diesterquats, and/or triesterquats), amide quaternary ammonium compounds (monoamide quats and/or diamide quats), imidazoline quaternary ammonium compounds, alkyl quaternary ammonium compounds (mono alkyl quats, dialkyl quats, trialkyl quats, and/or tetraalkyl quats), amidoester quaternary ammonium compounds, and mixtures thereof.

Non-limiting examples of suitable monoesterquats and diesterquats are selected from the group consisting of: bis-(2-hydroxypropyl)-dimethylammonium methylsulfate fatty acid ester and isomers of bis-(2-hydroxypropyl)-dimethylammonium methylsulfate fatty acid ester and/or mixtures thereof, 1,2-di(acyloxy)-3-trimethylammoniopropane chloride, N,N-bis(stearoyl-oxy-ethyl)-N,N-dimethyl ammonium chloride, N,N-bis(tallowoyl-oxy-ethyl) N,N-dimethyl ammonium chloride, bis(2-tallowoyloxyethyl)dimethyl ammonium chloride, N,N-bis(stearoyl-oxy-ethyl)-N-(2 hydroxyethyl)-N-methyl ammonium methylsulfate, N,N-bis-(stearoyl-2-hydroxypropyl)-N,N-dimethylammonium methylsulfate, N,N-bis-(tallowoyl-2-hydroxypropyl)-N,N-dimethylammonium methylsulfate, N,N-bis-(palmitoyl-2-hydroxypropyl)-N,N-dimethylammonium methylsulfate, N,N-bis-(stearoyl-2-hydroxypropyl)-N,N-dimethylammonium chloride, 1,2-di-(stearoyl-oxy)-3-trimethyl ammoniumpropane chloride, dicanoladimethylammonium chloride, di(hard)tallowdimethylammonium chloride, dicanoladimethylammonium methylsulfate, 1-methyl-1-stearoylamidoethyl-2-stearoylimidazolinium methylsulfate, 1-tallowylamidoethyl-2-tallowylimidazoline, dipalmylmethyl hydroxyethylammonium methylsulfate, and mixtures thereof.

In one example, the surface softening active has the following formula (1):

$$\{R_{4-m}-N^+-[R^4-Y-R^1]_m\}X^- \quad (1)$$

wherein each R comprises either hydrogen, a short chain $C_1$-$C_6$, for example a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each $R^4$ is independently $(CH_2)_n$, $CH_2$-$CH(CH_3)$— or $CH$—$(CH_3)$—$CH_2$—; each Y may comprise —O—(O)C—, —C(O)—O—, —NR—C(O)—, or —C(O)—NR—; each m is 2 or 3; each n is from 1 to about 4, in one aspect 2; the sum of carbons in each $R^1$, plus one when Y is —O—(O)C— or —NR—C(O)—, may be $C_{12}$-$C_{22}$, for example $C_{14}$-$C_{20}$, with each $R^1$ being a hydrocarbyl, or substituted hydrocarbyl group; and $X^-$ may comprise any softener-compatible anion. In one aspect, the softener-compatible anion may comprise chloride, bromide, methylsulfate, ethylsulfate, sulfate, and nitrate. In another example, the softener-compatible anion ($X^-$) may be chloride or methyl sulfate.

An example of a suitable surface softening agent is a "propyl" ester quaternary ammonium surface softening agent, for example 1,2-di(acyloxy)-3-trimethylammoniopropane chloride.

In another example, the surface softening agent has the formula (4):

$$[R_{4-m}-N^+-R^1_m]X^- \quad (4)$$

wherein each R, $R^1$, m are as disclosed above, and $X^-$ may comprise any softener-compatible anion. In one aspect, the softener-compatible anion may comprise chloride, bromide, methylsulfate, ethylsulfate, sulfate, and nitrate. In another example, the softener-compatible anion ($X^-$) may comprise chloride or methyl sulfate.

Non-limiting examples of surface softening agents include N,N-bis(stearoyl-oxy-ethyl)-N,N-dimethyl ammonium chloride, N,N-bis(tallowoyl-oxy-ethyl)-N,N-dimethyl ammonium chloride, N,N-bis(stearoyl-oxy-ethyl)-N-(2-hydroxyethyl)-N-methyl ammonium methylsulfate.

A non-limiting example of a surface softening agent includes 1,2-di-(stearoyl-oxy)-3-trimethyl ammoniumpropane chloride.

Non-limiting examples of surface softening agents include dialkylenedimethylammonium salts such as dicanoladimethylammonium chloride, di(hard)tallowdimethylammonium chloride dicanoladimethylammonium methylsulfate, and mixtures thereof. An example of commercially available dialkylenedimethylammonium salts usable in the present invention is dioleyldimethylammonium chloride available from Witco Corporation under the trade name Adogen® 472 and dihardtallow dimethylammonium chloride available from Akzo Nobel Arquad 2HT75.

A non-limiting example of a surface softening agent includes 1-methyl-1-stearoylamidoethyl-2-stearoylimidazolinium methylsulfate available commercially from the Witco Corporation under the trade name Varisoft®.

A non-limiting example of a surface softening agent includes 1-tallowylamidoethyl-2-tallowylimidazoline.

Non-limiting examples of surface softening agents include reaction products of fatty acids with diethylenetriamine, for example in a molecular ratio of about 2:1, said reaction product mixture containing N,N"-dialkyldiethylenetriamine with the formula:

$$R^1-C(O)-NH-CH_2CH_2-NH-CH_2CH_2-NH-C(O)-R^1$$

wherein $R^1$ is an alkyl group of a commercially available fatty acid derived from a vegetable or animal source, such as Emersol® 223LL or Emersol® 7021, available from Henkel Corporation. In one example, the fatty acid may be obtained, in whole or in part, from a renewable source, via extraction from plant material, fermentation from plant material, and/or obtained via genetically modified organisms such as algae or yeast.

A non-limiting example of a surface softening agent includes a di-fatty amidoamine based surface softening agent having the formula:

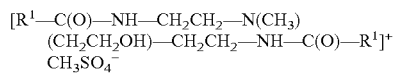

wherein $R^1$ is an alkyl group. An example of such a surface softening agent is commercially available from the Witco Corporation e.g. under the trade name Varisoft® 222LT.

Non-limiting examples of surface softening agents include reaction products of fatty acids with N-2-hydroxyethylethylenediamine, for example in a molecular ratio of about 2:1, said reaction product mixture containing a compound of the formula:

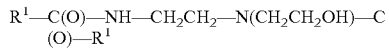

wherein $R^1$—C(O) is an alkyl group of a commercially available fatty acid derived from a vegetable or animal source, such as Emersol® 223LL or Emersol® 7021, available from Henkel Corporation.

A non-limiting example of a surface softening agent includes a dialkyl imidazoline diester compound, where the compound is the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid or a mixture of the above.

In one example, the surface softening agent is selected from the group consisting of: ditallowoyloxyethyl dimethyl ammonium chloride, dihydrogenated-tallowoyloxyethyl dimethyl ammonium chloride, ditallow dimethyl ammonium chloride, dihydrogenatedtallow dimethyl ammonium chloride, ditallowoyloxyethyl methylhydroxyethylammonium methyl sulfate, dihydrogenated-tallowoyloxyethyl methyl hydroxyethylammonium chloride, and mixtures thereof.

As used herein, the term "polyhydroxy compound(s)" is defined as a chemical agent that imparts lubricity or emolliency to tissue paper products and also possesses permanence with regard to maintaining the fidelity of its deposits without substantial migration when exposed to the environmental conditions to which products of this type are ordinarily exposed during their typical life cycle. The present invention contains as an essential component from about 2.0% to about 30.0%, preferably from 5% to about 20.0%, more preferably from about 8.0% to about 15.0%, of a water soluble polyhydroxy compound, based on the dry fiber weight of the tissue paper.

Non-limiting examples of water soluble polyhydroxy compounds suitable for use in the present invention include glycerol, polyglycerols having a weight average molecular weight of from about 150 to about 800 and polyoxyethylene glycol and polyoxypropylene glycol having a weight-average molecular weight of from about 200 to about 4000, preferably from about 200 to about 1000, most preferably from about 200 to about 600. Polyoxyethylene glycol having a weight average molecular weight of from about 200 to about 600 are especially preferred. Mixtures of the above-described polyhydroxy compounds may also be used. For example, mixtures of glycerol and polyglycerols, mixtures of glycerol and polyoxyethylene glycols, 'mixtures of polyglycerols and polyoxyethylene glycols/oxides, etc. are useful in the present invention. A particularly preferred polyhydroxy compound is polyoxyethylene glycol having a weight average molecular weight of about 200. This material is available commercially from The Dow Chemical Company under the trade name "Carbowax™ 200."

Specific examples of ester-functional quaternary ammonium compounds having the structures detailed above and suitable for use in the present invention may include the diester dialkyl dimethyl ammonium salts such as diester ditallow dimethyl ammonium chloride, monoester ditallow dimethyl ammonium chloride, diester ditallow dimethyl ammonium methyl sulfate, diester di(hydrogenated)tallow dimethyl ammonium methyl sulfate, diester di(hydrogenated)tallow dimethyl ammonium chloride, and mixtures thereof, for example diester ditallow dimethyl ammonium chloride and/or diester di(hydrogenated)tallow dimethyl ammonium chloride, which are commercially available from Witco Chemical Company Inc. of Dublin, Ohio under the tradename "ADOGEN SDMC".

The surface softening agent may exhibit an Iodine Value of between 0-140 and/or from about 5 to about 100 and/or from about 10 to about 80 and/or from about 15 to about 70 and/or from about 18 to about 60 and/or from about 18 to about 25. In one example, when the surface softening agent is a partially hydrogenated fatty acid quaternary ammonium compound it exhibits a Iodine Value of from about 25 to about 60.

In one example, the surface softening composition of the present invention comprises two or more different surface softening agents, for example two or more different quaternary ammonium compounds and/or at least one quaternary ammonium compound and at least one silicone polymer. When the neat surfactant component, for example surface softening composition comprises one or more surface softening agents, for example a quaternary ammonium compound and/or a silicone polymer, the surface softening agent may be present in the neat surfactant component at a level of from about 0.001% to about 10% and/or from about 0.1% to about 8% and/or from about 0.5% to about 5% by weight.

Non-limiting examples of suitable surface softening agents that can be present in the surface softening composition of the present invention can be selected from the group consisting of: polymers such as polyethylene and derivatives thereof, hydrocarbons, waxes, oils, silicones, organosilicones (oil compatible), quaternary ammonium compounds, fluorocarbons, substituted $C_{10}$-$C_{22}$ alkanes, substituted $C_{10}$-$C_{22}$ alkenes, in particular derivatives of fatty alcohols and fatty acids(such as fatty acid amides, fatty acid condensates and fatty alcohol condensates), polyols, derivatives of polyols (such as esters and ethers), sugar derivatives (such as ethers and esters), polyglycols (such as polyethyleneglycol), and mixtures thereof.

In one example, the surface softening composition of the present invention is a microemulsion and/or a macroemulsion of a surface softening agent (for example an amino-functional polydimethylsiloxane, specifically an aminoethylaminopropyl polydimethylsiloxane) in water. In such an example, the concentration of the surface softening agent within the surface softening composition may be from about 3% to about 60% and/or from about 4% to about 50% and/or from about 5% to about 40%. Non-limiting examples of such microemulsions are commercially available from Wacker Chemie (MR1003, MR103, MR102). A non-limiting example of such a macroemulsion is commercially available from Momentive, Columbus, Ohio (CM849).

Non-limiting examples of suitable waxes may be selected from the group consisting of: paraffin, polyethylene waxes, beeswax, and mixtures thereof.

Non-limiting examples of suitable oils may be selected from the group consisting of: mineral oil, silicone oil, silicone gels, petrolatum, and mixtures thereof.

Non-limiting examples of suitable silicones may be selected from the group consisting of: polydimethylsiloxanes, aminosilicones, cationic silicones, quaternary silicones, silicone betaines, and mixtures thereof.

In one example, the surface softening agent comprises a partially hydrogenated tallow diester chloride quaternary ammonium compound, for example bis(2-tallowoyloxyethyl)dimethyl ammonium chloride, premixed with polyethylene glycol, for example PEG 400. For example, the premix is about 70-75% quaternary ammonium compound (such as Adogen SDMC-type from Witco Corporation and 25-30% PEG 400, available from J. T. Baker Company of Phillipsburg, N.J.).

The surface softening composition may comprise additional ingredients such as a vehicle as described herein below which may not be present on the fibrous structure and/or sanitary tissue product comprising such fibrous structure. In one example, the surface softening composition may comprise a surface softening agent and a vehicle such as water to facilitate the application of the surface softening agent onto the surface of the fibrous structure.

It is understood that combinations of any of the surface softening agents disclosed herein are suitable for use in the surface softening compositions of the present invention.

Non-Limiting Examples

Example 1

A first stock chest of 100% *eucalyptus* fiber is prepared with a conventional pulper to have a consistency of about 3.0% by weight. The thick stock of the first hardwood chest is directed through a thick stock line where a wet-strength additive, HERCOBOND 1194 (commercially available from Ashland Inc.), a temporary wet strength agent, is added in-line to the thick stock at about 0.5 lbs. per ton of dry fiber as it moves to the first fan pump.

Additionally, a second stock chest of 100% *eucalyptus* fiber is prepared with a conventional pulper to have a consistency of about 3.0% by weight. The thick stock of the second hardwood chest is directed through a thick stock line where a wet-strength additive, HERCOBOND 1194, is added in-line to the thick stock at about 0.5 lbs. per ton of dry fiber as it moves to the second fan pump.

A third stock chest is prepared with 100% NSK fiber with a final consistency of about 3.0%. The blended thick stock is directed to a disk refiner where it is refined to a Canadian Standard Freeness of about 580 to 625. The NSK thick stock of the third stock chest is then directed through a thick stock line where a wet-strength additive, HERCOBOND 1194, is added to the thick stock at about 1.5 lbs. per ton of dry fiber. The refined, 100% NSK thick stock is then directed to a third fan pump.

The *eucalyptus* fiber slurry diluted by the first fan pump is directed through the bottom headbox chamber (Yankee-side layer). The NSK fiber slurry diluted by the third fan pump is directed through the center headbox chamber. The *eucalyptus* fiber slurry diluted by the second fan pump directed to the top headbox chamber (Fabric-side) and delivered in superposed relation to the fixed-roof former's forming wire to form thereon a three-layer embryonic web, of which about 34.5% of the top side is made up of pure *eucalyptus* fibers, center is made up of about 34.5% of a NSK fiber and the bottom side (Yankee-side) is made up of about 34.5% of pure *eucalyptus* fiber. Dewatering occurs through the outer wire and the inner wire and is assisted by wire vacuum boxes. Forming wire is an 84M design traveling at a speed of 800 fpm (feet per minute).

The embryonic wet web is transferred from the carrier (inner) wire, at a fiber consistency of about 24% at the point of transfer, to a patterned drying fabric. The speed of the patterned drying fabric is about 800 fpm (feet per minute). The drying fabric is designed to yield a pattern of substantially machine direction oriented linear channels having a continuous or semi-continuous network of high density (knuckle) areas. This drying fabric is formed by casting an impervious resin surface onto a fiber mesh supporting fabric. The supporting fabric is a 127×52 filament, dual layer mesh. The thickness of the resin cast is about 12 mils above the supporting fabric.

While remaining in contact with the patterned drying fabric, the web is pre-dried by air blow-through pre-dryers to a fiber consistency of about 60% by weight.

After the pre-dryers, the semi-dry web is transferred to the Yankee dryer through a nip formed by the pressure roll surface and the Yankee surface where the Yankee surface has been pre-treated with a sprayed a creping adhesive coating. The coating is a blend consisting of Georgia Pacific's UNICREPE 457T20 and Vinylon Works' VINYLON 8844 at a ratio of about 92 to 8, respectively. The fiber consistency is increased to about 97% before the web is dry creped from the Yankee with a doctor blade.

The web is removed from the Yankee surface by a creping blade having a bevel angle of about 25 degrees and is positioned with respect to the Yankee dryer to provide an impact angle of about 81 degrees. The Yankee dryer is operated at a temperature of about 350° F. (177° C.) and a speed of about 800 fpm. The fibrous structure is wound in a roll using a surface driven reel drum having a surface speed of about 700 fpm (feet per minute) to make a parent roll.

During a converting process, one or more neat surfactant components, for example described herein, such as cocoamidopropyl betaine, is applied, for example with a slot extrusion die, to the outside surface of the fibrous structure as the parent roll is unwound and converted into a finished fibrous structure and/or sanitary tissue product. If a multi-ply sanitary tissue product is desired, then two or more of the fibrous structure plies or at least one with a different fibrous structure ply can be bonded together to form a multi-ply sanitary tissue product.

Example 2

A fibrous structure is made according to Example 1. During a converting process, one or more neat surfactant components of the present invention, such as lauryl lactate, is applied, for example with a slot extrusion die, for example at a rate of about 20% by weight, to the outside surface of the fibrous structure as the parent roll is unwound and converted into a finished fibrous structure and/or sanitary tissue product. If a multi-ply sanitary tissue product is desired, then two or more of the fibrous structure plies or at least one with a different fibrous structure ply can be bonded together to form a multi-ply sanitary tissue product.

Example 3

The individual plies of Example 3 are made according to the process detailed in Example 1 supra. Two plies were combined with the wire side facing out. During the converting process, a surface softening agent and a lotion are applied sequentially with slot extrusion dies to the outside surface of both plies. The surface softening agent is a formula comprising one or more polyhydroxy compounds (Polyethylene glycol, Polypropylene glycol, and/or copolymers thereof marketed by BASF Corporation of Florham Park, N.J.), glycerin (marketed by PG Chemical Company), and silicone (i.e. MR-1003, marketed by Wacker Chemical Corporation of Adrian, Mich.). The surface softening agent is applied to the web at a rate of 14.1% by weight and the lotion is applied to the web at a rate of 5.0% by weight. The plies are then bonded together with mechanical ply-bonding wheels, slit, and then folded into finished 2-ply facial tissue product. Each user unit tested in accordance with the test methods described *supra*.

Example 4

The individual plies of Example 4 are made according to the process detailed in Example 1 supra. Two plies were combined with the wire side facing out. During the converting process, a surface softening agent and a lotion are applied sequentially with slot extrusion dies to the outside surface of both plies. The surface softening agent is a formula comprising one or more polyhydroxy compounds (Polyethylene glycol, Polypropylene glycol, and/or copolymers thereof marketed by BASF Corporation of Florham Park, N.J.), glycerin (marketed by PG Chemical Company), and silicone (i.e. MR-1003, marketed by Wacker Chemical Corporation of Adrian, MI). The surface softening agent is applied to the web at a rate of 10.0% by weight and the lotion is applied to the web at a rate of 5.0% by weight. The plies are then bonded together with mechanical ply-bonding wheels, slit, and then folded into finished 2-ply facial tissue product. Each user unit tested in accordance with the test methods described *supra*.

Example 5

The individual plies of Example 5 are made according to the process detailed in Example 1 supra. Two plies were combined with the wire side facing out. During the converting process, a surface softening agent and a lotion are applied sequentially with slot extrusion dies to the outside surface of both plies. The surface softening agent is a formula comprising one or more polyhydroxy compounds (Polyethylene glycol, Polypropylene glycol, and/or copolymers thereof marketed by BASF Corporation of Florham Park, NJ), glycerin (marketed by PG Chemical Company), and silicone (i.e. MR-1003, marketed by Wacker Chemical Corporation of Adrian, MI). The surface softening agent is applied to the web at a rate of 10.0% by weight and the lotion is applied to the web at a rate of 10.4% by weight. The plies are then bonded together with mechanical ply-bonding wheels, slit, and then folded into finished 2-ply facial tissue product. Each user unit tested in accordance with the test methods described *supra*.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary tissue product comprising an embossed wet-laid fibrous structure, wherein the sanitary tissue product comprises an exterior surface comprising a neat surfactant component and a surface softening composition wherein the neat surfactant component comprises one or more neat surfactants free from dilution, encapsulation and emulsion such that the one or more neat surfactants are applied to a user's skin during use of the sanitary tissue product, and wherein the neat surfactant component is present on at least a portion of the exterior surface of the sanitary tissue product, and wherein the surface softening composition comprises a surface softening agent that is at least one of: silicones, quaternary ammonium compounds, polyhydroxy compounds and mixtures thereof, wherein the surface softening composition is present on the wet-laid fibrous structure between a surface of the wet-laid fibrous structure and the neat surfactant component;

wherein the wet-laid fibrous structure is embossed;

wherein the embossed wet-laid fibrous structure comprises a plurality of fibrous elements.

2. The sanitary tissue product according to claim 1 wherein the neat surfactant component comprises two or more neat surfactants.

3. The sanitary tissue product according to claim 1 wherein at least one of the one or more neat surfactants is selected from the group consisting of: neat nonionic surfactants, neat anionic surfactants, neat amphoteric surfactants, neat zwitterionic surfactants, cationic surfactants, and mixtures thereof.

4. The sanitary tissue product according to claim 1 wherein the neat surfactant component is present on the exterior surface of the sanitary tissue product at a level of at least 0.0001% by weight of the fibrous structure.

5. The sanitary tissue product according to claim 1 wherein the exterior surface comprises two or more neat surfactant components present thereon.

6. The sanitary tissue product according to claim 1 wherein the plurality of fibrous elements comprises a plurality of fibers.

7. The sanitary tissue product according to claim 6 wherein the plurality of fibers comprises pulp fibers.

8. The sanitary tissue product according to claim 7 wherein the pulp fibers comprise wood fibers.

9. The sanitary tissue product according to claim 6 wherein the plurality of fibers comprises a plurality of synthetic fibers.

10. The sanitary tissue product according to claim 1 wherein the plurality of fibrous elements comprises a plurality of filaments.

11. The sanitary tissue product according to claim 1 wherein the embossed wet-laid fibrous structure is an embossed, through-air-dried wet-laid fibrous structure.

12. The sanitary tissue product according to claim 1 wherein the embossed wet-laid fibrous structure is an embossed, conventional wet pressed wet-laid fibrous structure.

13. The sanitary tissue product according to claim 1 wherein the embossed wet-laid fibrous structure is an embossed, belt creped wet-laid fibrous structure.

14. The sanitary tissue product according to claim 1 wherein the embossed wet laid fibrous structure is an embossed, fabric creped wet-laid fibrous structure.

15. The sanitary tissue product according to claim 1 wherein the embossed wet-laid fibrous structure comprises embossed areas containing the neat surfactant component and non-embossed areas that are void of the neat surfactant component.

16. A roll of sanitary tissue product comprising the sanitary tissue product according to claim 1.

17. A multi-ply sanitary tissue product comprising a first fibrous structure ply comprising a sanitary tissue product according to claim 1 and a second fibrous structure ply.

18. A method for making a sanitary tissue product according to claim 1 wherein the method comprises the steps of applying a surface softening composition to a surface of a wet-laid embossed fibrous structure; and applying a neat surfactant component to a surface of an embossed wet-laid fibrous structure wherein the neat surfactant component comprises one or more neat surfactants free from dilution, encapsulation and emulsion to the surface softening composition such that the surface softening composition is present between the neat surfactant component and the surface of the wet-laid embossed fibrous structure such that the neat surfactant component forms an exterior surface of a sanitary tissue product comprising a wet-laid embossed fibrous structure.

19. A method for improving the removal of fecal matter from a user's skin, the method comprising the step of contacting a user's skin with a sanitary tissue product according to claim 1.

* * * * *